US009212548B2

(12) United States Patent
Vigneaux et al.

(10) Patent No.: US 9,212,548 B2
(45) Date of Patent: Dec. 15, 2015

(54) EQUIPMENT AND METHODS FOR DETERMINING WAITING-ON-CEMENT TIME IN A SUBTERRANEAN WELL

(75) Inventors: Pierre Vigneaux, Moisenay (FR); Nicolas Flamant, Montrouge (FR); Thomas Barrou, Cachan (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 268 days.

(21) Appl. No.: 13/993,322

(22) PCT Filed: Dec. 7, 2011

(86) PCT No.: PCT/EP2011/006369
§ 371 (c)(1),
(2), (4) Date: Jul. 22, 2013

(87) PCT Pub. No.: WO2012/079768
PCT Pub. Date: Jun. 21, 2012

(65) Prior Publication Data
US 2013/0306308 A1    Nov. 21, 2013

(30) Foreign Application Priority Data

Dec. 17, 2010 (EP) .................................. 10195826

(51) Int. Cl.
*E21B 47/12* (2012.01)
*E21B 33/14* (2006.01)
*E21B 47/00* (2012.01)
*G01L 1/24* (2006.01)

(52) U.S. Cl.
CPC ................. *E21B 47/12* (2013.01); *E21B 33/14* (2013.01); *E21B 47/00* (2013.01); *E21B 47/0005* (2013.01); *E21B 47/123* (2013.01); *G01L 1/246* (2013.01)

(58) Field of Classification Search
CPC ......... E21B 33/14; E21B 47/00; E21B 47/12; E21B 47/123
See application file for complete search history.

(56) References Cited

U.S. PATENT DOCUMENTS

| 6,041,872 | A  | * | 3/2000  | Holcomb ........................ 175/40 |
| 6,555,807 | B2 |   | 4/2003  | Clayton et al. |
| 6,913,079 | B2 |   | 7/2005  | Tubel |
| 7,687,764 | B1 |   | 3/2010  | Knapp |
| 8,515,096 | B2 | * | 8/2013  | Seltzer et al. ................ 381/94.1 |
| 2004/0047534 | A1 | * | 3/2004 | Shah et al. ...................... 385/12 |
| 2004/0083058 | A1 |   | 4/2004 | Ravi et al. |
| 2010/0254650 | A1 |   | 10/2010 | Rambow |

FOREIGN PATENT DOCUMENTS

| EP | 1854959 | 11/2007 |
| WO | 2009/127328 | 10/2009 |

OTHER PUBLICATIONS

B. Piot and G. Cuvillier, "Primary Cementing Technique," Nelson E.B. and Guillot D. (eds) Well Cementing—2nd Edition, Houston, Schlumberger (2006): 459-501.

* cited by examiner

Primary Examiner — William P Neuder

(57) ABSTRACT

Improved equipment and methods for determining the waiting-on-cement time after a cementing operation involve an optic-fiber coil that immersed in the cement slurry downhole. The intensity of a reflected light signal from the coil is monitored versus time. Attenuation of the reflected-light intensity corresponds to the development of gel strength, allowing operators to unambiguously determine when well-bore operations may recommence after a cement job. The optic-fiber coil is wound around a spool such that there is at least one coil crossing on the spool.

20 Claims, 2 Drawing Sheets

EQUIPMENT AND METHODS FOR DETERMINING WAITING-ON-CEMENT TIME IN A SUBTERRANEAN WELL

BACKGROUND

The statements in this section merely provide background information related to the present disclosure and may not constitute prior art.

This disclosure is related in general to wellbore-telemetry technology. In particular, it relates to means by which the setting time of a cement slurry in a wellbore may be determined remotely.

After a well is drilled, the conventional practice in the oil and gas industry consists of lining the well with a metal casing. An annular area is thus formed between the casing and the subterranean formation. A cementing operation is then conducted with the goal of filling the annular area with cement slurry. After the cement sets, the combination of casing and set cement strengthens the wellbore and provides hydraulic isolation between producing zones through which the well penetrates.

It is common to employ more than one string of casing in the wellbore. In this respect, a first string of casing is set in the wellbore when the well is drilled to a first designated depth. The first string of casing is hung from the surface, and then cement is circulated into the annulus behind the casing. The well is then drilled to a second designated depth, and a second string of casing, or a liner, is run into the well. The second string is set at a depth such that the upper portion of the second string of casing overlaps the lower portion of the first string of casing. The second liner string is then fixed or hung off of the existing casing. Afterwards, the second casing string is also cemented. This process is typically repeated with additional liner strings until the well has been drilled to total depth. In this manner, wells are typically formed with two or more strings of casing of an ever-decreasing diameter.

The well cementing process typically involves the use of wiper plugs. Wiper plugs are elongated elastomeric bodies that are used to separate fluids as they travel through the casing interior. This practice prevents performance difficulties that may occur if the various fluids commingle. Usually the cementing operation requires two wiper plugs. When the cement slurry is ready to be dispensed, a first plug is released into the casing. The cement slurry is pumped behind the plug, thereby moving the plug downhole. At the bottom of the casing string, the first plug seats against a float valve, thereby closing off flow through the float valve. Hydraulic pressure builds above the first plug until it is sufficient to cause a membrane in the first plug to rupture. Thereafter, cement slurry flows through the first plug and the float valve, and up into the annular space between the wellbore and the casing string.

After a sufficient amount of cement slurry has been placed into the wellbore, a second wiper plug is deployed. A displacement fluid is pumped behind the second plug to move the second plug down the casing string, whereupon it lands upon the first plug. Unlike the first plug, the second plug does not have a membrane; therefore, the second plug seals the interior of the casing from the annular space between the wellbore and the casing string.

A thorough discussion of the primary cementing process may be found in the following publication: Piot B. and Cuvillier G.: "Primary Cementing," in Nelson E. B. and Guillot D. (eds.): *Well Cementing—$2^{nd}$ Edition*, Houston: Schlumberger (2006): 459-501.

After completing the cement-placement process, it is usually necessary to delay further wellbore operations for a time sufficient to allow the cement slurry to set and gain sufficient strength. Strength, is required to support the casing and provide zonal isolation. This idle time period is usually called the "waiting-on-cement" or WOC time. Traditionally, operators estimate the WOC time from pre-job laboratory testing. The cement slurry is placed in a pressurized curing chamber, and the time necessary for the slurry to set and develop sufficient strength is measured. Such measurements may be performed by crushing set-cement cubes after certain curing periods, or by continuously monitoring the sonic transit time through the cement slurry and calculating its strength.

The curing conditions for laboratory testing are usually estimated from field data provided by the well operator, temperature schedules based on the geothermal gradient, or both. The accuracy of these data are subject to several variables, including the temperature of the cement-slurry ingredients at the surface and the duration of time during which the well has been circulated and cooled before the cement job. The uncertainty may be further exaggerated when the casing string or liner is very long, resulting in a significant temperature gradient between the top and bottom of the string.

Underestimating the WOC time, and re-commencing wellbore operations prematurely may result in well damage, loss of zonal isolation or both. Overestimating the WOC time may result in unproductive rig time. In certain remote environments such as offshore platforms, rig time is usually very expensive, and halting well operations for an excessive period of time may be costly.

As a result, despite valuable contributions in the art, means by which the WOC time may be determined directly and unambiguously would be valuable. Such means would give operators more confidence when deciding to recommence wellbore operations.

SUMMARY

In an aspect, embodiments relate to methods for determining the set time of a cement slurry in a subterranean wellbore.

Embodiments pertain to equipment where a continuous fiber-optic line is selected that has a first end and a second end. The first end is secured to a fixed position. The fixed position may be at the top of the well and connected to a measuring device. The second end of the line is secured to a spool, and the rest of the line is wound around the spool. Sufficient line is present such that, when the cement-slurry set time is determined, there is at least one fiber-line crossing on the spool. The spool is preferably immersed in the cement slurry. A light signal is generated from the fixed position and transmitted along the fiber-optic line. The intensity of the reflected light signal is measured, thereby informing on the nature of the cement slurry in which the spool is immersed.

In further embodiments, a continuous fiber-optic line is selected that has a first end and a second end. The first end is secured to a fixed position. The fixed position may be at the top of the well and connected to a measuring device. The second end of the line is secured to a spool, and the rest of the line is wound around the spool. Sufficient line is present such that, when the cement-slurry set time is determined, there is at least one fiber-line crossing on the spool. The spool is placed inside an apparatus for dispensing line. The apparatus is attached to a device that travels through a tubular body in the wellbore, and both are inserted inside the tubular body.

Cement slurry is then pumped inside the tubular body, releasing the device, and causing the device to travel through the tubular body and away from the fixed position. The line unwinds from the apparatus as the device moves away from the fixed position. A volume of cement slurry is pumped behind the device such that the apparatus and the spool are immersed in the cement slurry. A process fluid is then pumped behind the cement slurry until the device rests at a desired location inside the tubular body.

A light signal is generated from the fixed position and transmitted along the fiber-optic line. The intensity of the reflected light signal is measured, thereby informing on the nature of the cement slurry in which the spool is immersed.

In yet further embodiments, a continuous fiber-optic line is selected that has a first end and a second end. The first end is secured to a fixed position. The fixed position may be at the top of the well and connected to a measuring device. The second end of the line is secured to a spool, and the rest of the line is wound around the spool. Sufficient line is present such that, when the cement-slurry set time is determined, there is at least one fiber-line crossing on the spool. The spool is placed inside a sealable chamber. The chamber is filled with the cement slurry, and the chamber containing the fiber spool is sealed. The chamber is then installed in the well such that the cement slurry inside the chamber experiences the same curing conditions as the slurry in the subterranean wellbore.

A light signal is generated from the fixed position and transmitted along the fiber-optic line. The intensity of the reflected light signal is measured, thereby informing on the nature of the cement slurry in which the spool is immersed. The sealed chamber may preferably travel down the well by force of gravity.

DETAILED DESCRIPTION

Figure 1:
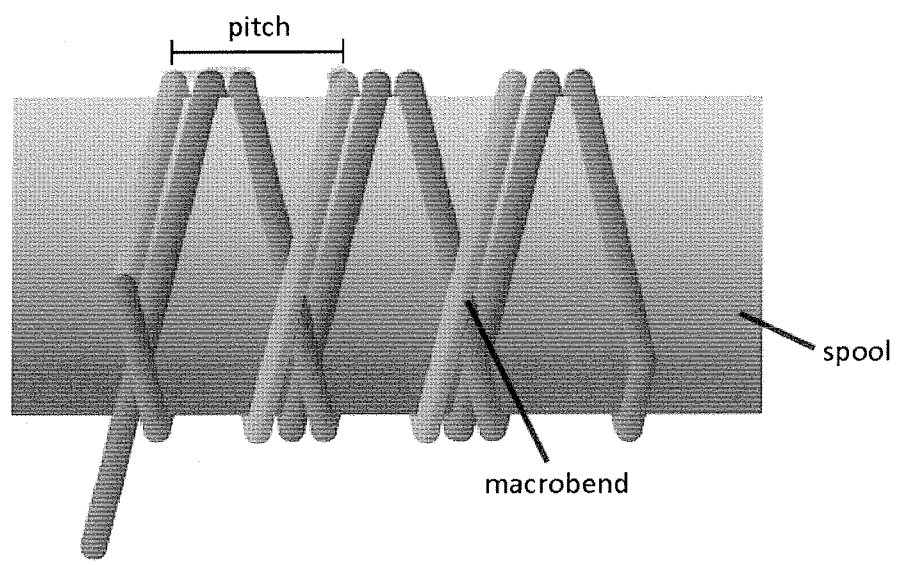
FIG. 1 is an illustration showing fiber line coiled around a spool, the pitch of the fiber coil and fiber macrobends.

The disclosure pertains to treatment of vertical wells, but is equally applicable to wells of any orientation. The disclosure mainly describe hydrocarbon production wells, but it is to be understood that it may be equally applicable to wells for production of other fluids, such as water or carbon dioxide or, for example, for injection or storage wells. This disclosure is applicable both to offshore and land wells. It should also be understood that throughout this specification, when a concentration or amount range is described as being useful, or suitable, or the like, it is intended that any and every concentration or amount within the range, including the end points, is to be considered as having been stated. Furthermore, each numerical value should be read once as modified by the term "about" (unless already expressly so modified) and then read again as not to be so modified unless otherwise stated in context. For example, "a range of from 1 to 10" is to be read as indicating each and every possible number along the continuum between about 1 and about 10. In other words, when a certain range is expressed, even if only a few specific data points are explicitly identified or referred to within the range, or even when no data points are referred to within the range, it is to be understood that the inventor appreciates and understands that any and all data points within the range are to be considered to have been specified, and that the inventor has possession of the entire range and all points within the range.

The following disclosure aims at cement by it is to be understood that any other settable composition might be envisaged, geopolymers is an example of another type of setting compositions.

In recent years, the deployment of fiber lines in subterranean wellbores has become increasingly frequent. The most common application is to install optical fiber as a conduit through which various downhole measurements may be performed. Such measurements include temperature, pressure, pH, density, resistivity, conductivity, salinity, carbon-dioxide concentration, asphaltene concentration, etc. Today, optical-fiber technologies may be employed throughout the lifetime of a well—drilling, completion, stimulation, production surveillance and even after abandonment.

Optical fibers may be deployed in several ways. For example, the fiber line may be preinstalled in equipment and tools and lowered into the well, it may be pumped downhole such that it unfurls as it follows the fluid down the well, and it may be lowered into the wellbore in the same manner as wireline.

It may be desirable to perform some of the aforementioned measurements during well-cementing operations. Under these circumstances, optical fiber line may be deployed during primary cementing by attaching it to a wiper plug. A number of methods have been described. One method involves a spool of fiber line, with one end of the fiber connected to the wiper plug. The spool remains at the top of the well, either inside or outside the wellhead. The spool dispenses fiber line as the wiper plug travels through the casing string. A second method attaches the fiber-line spool to the wiper plug, with one end of the fiber attached to the wellhead. The spool unfurls fiber as the plug travels through the casing string. A third method involves fixing fiber spools to both the top of the well and on the fiber plug. Such a configuration reduces drag and allows for smoother fiber deployment.

In the context of well cementing, the fiber line may be employed to determine the location of the cement plug or to perform measurements that inform the well operator about the condition of the cement slurry. For example, a temperature sensor may be installed at the end of the fiber line that contacts the cement slurry downhole. The sensor could be used to detect the exothermic reaction that occurs when the cement slurry begins to set. Unfortunately, such exotherms may be masked or difficult to discern, because the temperature rise in the annular region resulting from the discontinuation of fluid circulation. The exotherm resulting from cement setting may also be difficult to detect in high-temperature wells. Therefore, using temperature as an indicator for the WOC time may not be sufficiently reliable.

However, cement setting is also accompanied by a mechanical effect—cement-matrix shrinkage. Such shrinkage exerts stress on the cement matrix, and the inventors have surprisingly discovered that an optical-fiber line may be employed to detect shrinkage. This measurement may be less ambiguous and may provide a more accurate determination of the WOC time.

The shrinkage measurement requires the presence of uncoiled optical fiber on a fiber-line spool that is immersed in the cement slurry. The fiber should also be coiled at a pitch that is greater than the fiber diameter. As shown in FIG. 1, the term "pitch" refers to the distance between two consecutive strands of fiber on the spool. The fiber coil also presents a number of crossings that is a monotonic function of the coiling pitch. When the slurry surrounding the fiber coil begins to set, the resulting shrinkage tends to squeeze the coil, reducing the radius of the macrobends at the fiber crossings.

The macrobend-radius reduction may be detected by illuminating the fiber coil with light at a wavelength that is preferably between about 400 nm and 1700 nm. The intensity of the light becomes attenuated as the radius decreases. Using a mathematical model, the light attenuation may then be correlated with gel-strength development. The WOC time is the moment at which the cement-slurry gel strength is sufficiently high to provide casing support and zonal isolation.

Embodiments relate to methods for determining the set time of a cement slurry in a subterranean wellbore.

In Embodiment, a continuous fiber-optic line is selected that has a first end and a second end. The first end is secured to a fixed position. The fixed position may be at the top of the well and connected to a measuring device. The second end of the line is secured to the end of a spool, and the rest of the line is wound around the spool. Sufficient line is present such that, when the cement-slurry set time is determined, there is at least one fiber-line crossing on the spool. The spool is immersed in the cement slurry. A light signal is generated from the fixed position and transmitted along the fiber-optic line. The intensity of the reflected light signal is measured, thereby informing on the nature of the cement slurry in which the spool is immersed.

In further embodiments, a continuous fiber-optic line is selected that has a first end and a second end. The first end is secured to a fixed position. The fixed position may be at the top of the well and connected to a measuring device. The second end of the line is secured to the end of a spool, and the rest of the line is wound around the spool. Sufficient line is present such that, when the cement-slurry set time is determined, there is at least one fiber-line crossing on the spool. The spool is placed inside an apparatus for dispensing line. The apparatus is attached to a device that travels through a tubular body in the wellbore, and both are inserted inside the tubular body. The device may be (but would not be limited to) a cementing plug or a dart. The tubular body may be (but would not be limited to) casing, liner, drill pipe and coiled tubing.

Cement slurry is then pumped inside the tubular body, releasing the device, and causing the device to travel through the tubular body and away from the fixed position. The line unwinds from the apparatus as the device moves away from the fixed position. A volume of cement slurry is pumped behind the device such that the apparatus and the spool are immersed in the cement slurry. A process fluid is then pumped behind the cement slurry until the device rests at a desired location inside the tubular body. The process fluid may be (but would not be limited to) drilling fluid, cement slurry, spacer fluid, chemical wash and displacement fluid. The desired location may be the casing shoe.

A light signal is generated from the fixed position and transmitted along the fiber-optic line. The intensity of the reflected light signal is measured, thereby informing on the nature of the cement slurry in which the spool is immersed.

In yet further embodiments, a continuous fiber-optic line is selected that has a first end and a second end. The first end is secured to a fixed position. The fixed position may be at the top of the well and connected to a measuring device. The second end of the line is secured to the end of a spool, and the rest of the line is wound around the spool. Sufficient line is present such that, when the cement-slurry set time is determined, there is at least one fiber-line crossing on the spool. The spool is placed inside a sealable chamber. The chamber is filled with the cement slurry, and the chamber containing the fiber spool is sealed. The chamber is then installed in the well such that the cement slurry inside the chamber experiences the same curing conditions as the slurry in the subterranean wellbore.

A light signal is generated from the fixed position and transmitted along the fiber-optic line. The intensity of the reflected light signal is measured, thereby informing on the nature of the cement slurry in which the spool is immersed. The sealed chamber may be (but would not be limited to) a bomb, a dart, a sonde, a ball or a canister. The sealed chamber may preferably travel down the well by force of gravity.

For all embodiments, the cement slurry may be used in the context of primary cementing or remedial cementing.

For all embodiments, one or more sensors may be connected to the second end of the fiber line. In addition, a Bragg-grating sensor may be placed on one end of the fiber-optic line. The light signal may be generated and analyzed by an instrument that comprises a light transmitter and receiver.

The preceding description has been presented with reference to presently preferred embodiments. Persons skilled in the art and technology to which this disclosure pertains will appreciate that alterations and changes in the described structures and methods of operation can be practiced without meaningfully departing from the principle, and scope of the present disclosure. Accordingly, the foregoing description should not be read as pertaining only to the precise structures described and shown in the accompanying drawings, but rather should be read as consistent with and as support for the following claims, which are to have their fullest and fairest scope.

EXAMPLE

The following example serves to further illustrate the disclosure.

A cement slurry with the following composition was prepared. Class G cement+39% water by weight of cement. The following additives were mixed with the water: 0.27% by weight of water (BWOW) lignosulfonate-retarder solution, 1.38% BWOW polynaphthalene-sulfonate-dispersant solution, 1.38% BWOW sodium-silicate solution, 0.41% BWOW welan-gum antisettling agent, and 0.55% BWOW silicone antifoam agent. The slurry was used to cement a 40-cm (13⅜-in.) casing.

Two sensors were immersed downhole in the cement slurry: a thermocouple to measure simulated bottomhole temperature and a fiber-optic system that measured the intensity of the reflected light signal. The apparatus and the fiber optic deployment is described in detail in European Patent No. EP 1 854 959 B1.

Figure 2:
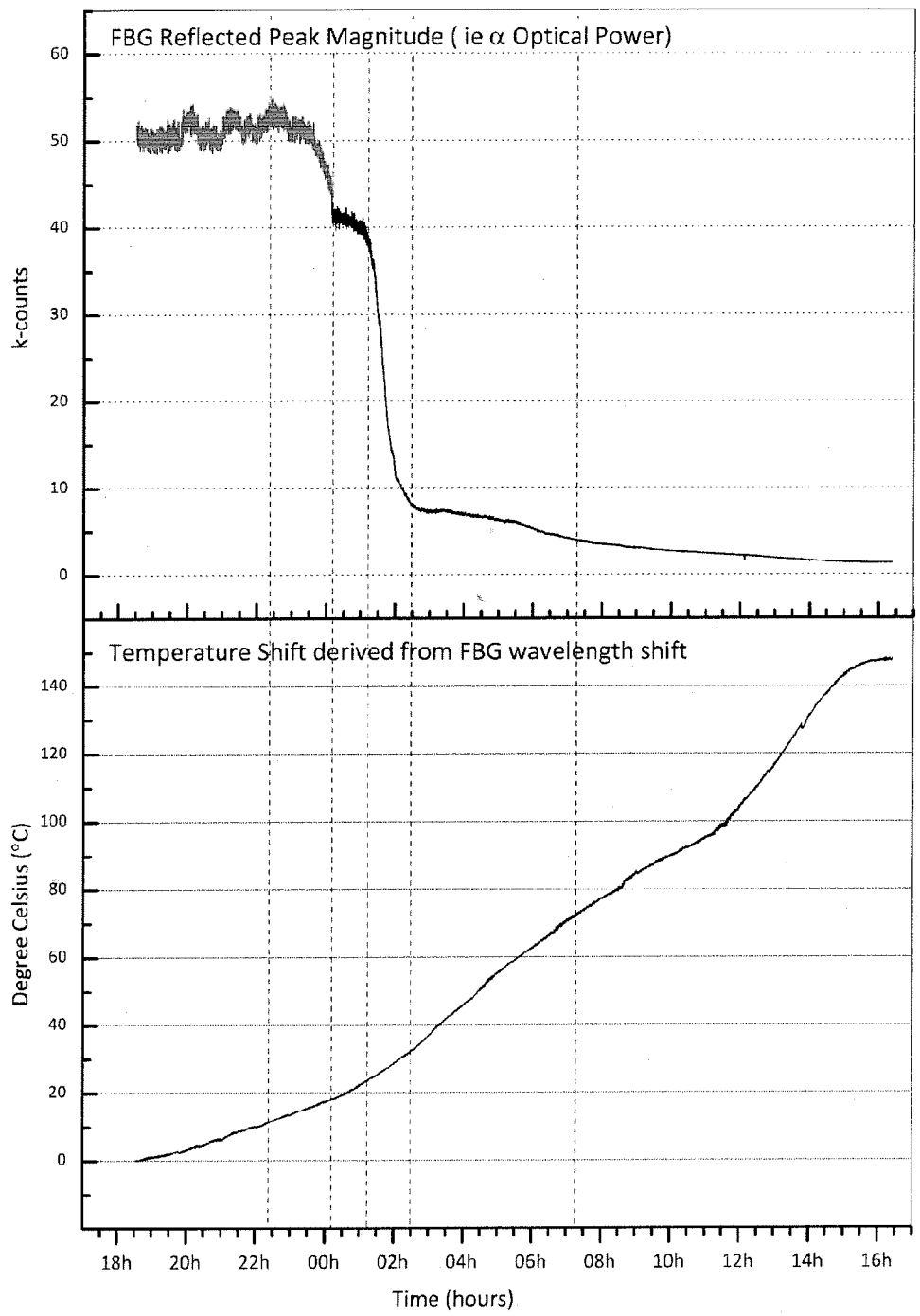
FIG. 2 is a plot showing measured downhole temperature versus the amplitude of the reflected light source measured through an optic-fiber line

The evolution of bottomhole temperature and reflected light intensity versus time is shown in FIG. 2. The signal from the optical sensor was read with an optical spectrum analyzer (OSA). At each acquisition step, the OSA outputs the intensity of the reflected signal versus its wavelength. The output shape was similar to a Gaussian distribution. An algorithm, e.g., the Levenberg Marquardt algorithm, was then used to identify the peak and its associated wavelength and intensity. In the present example, the wavelength was interpreted in terms of temperature and intensity.

FIG. 2 shows the 24-hr period after the end of displacement. Within this time period, the bottomhole temperature increased gradually with several subtle inflection points. It would be difficult to discern when the exotherm corresponding to cement setting commenced. However, the attenuation of the reflected light signal is not ambiguous. Between about 23:00 and 2:00, the intensity dropped from about 50,000 to about 7000 counts. This corresponds to a profound increase in gel strength. One may conclude that the duration of the WOC time was 8 hours, between 18:00 and 2:00.

The invention claimed is:

1. A method for determining set time of a cement slurry in a subterranean wellbore, comprising:
   (i) selecting a continuous fiber-optic line having a first end and a second end;
   (ii) securing the first end to a fixed position;
   (iii) securing the second end to a spool, and winding the line around the spool such that there is sufficient line to form at least one coil crossing when the set time is determined, and wherein a fiber-coil pitch in the spool is formed;
   (iv) immersing the spool in the cement slurry;
   (v) pumping a volume of cement slurry behind the spool;
   (vi) generating a light signal from the fixed position and transmitting the signal along the fiber-optic line; and
   (vii) measuring changes in the reflected-signal intensity, thereby informing on the state of the cement slurry in which the spool is immersed.

2. The method of claim 1, further comprising:
   (i) placing the spool in an apparatus for dispensing line;
   (ii) attaching the apparatus to a device that travels through a tubular body in the wellbore, and inserting both inside the tubular body;
   (iii) pumping cement slurry into the tubular body, releasing the device, allowing the device to travel through the tubular body, away from the fixed position, thereby allowing the line to unwind from the apparatus;
   (iv) pumping a volume of cement slurry behind the device such that the apparatus and the spool are immersed in the cement slurry; and
   (v) pumping process fluid behind the cement slurry, and allowing the device to rest at a desired location inside the tubular body.

3. The method of claim 1, further comprising:
   (i) placing the spool inside a sealable chamber;
   (ii) filling the chamber with the cement slurry and sealing the chamber with fiber spool inside;
   (iii) installing the chamber in the well, such that the cement slurry inside the chamber experiences the same curing conditions as the slurry in the subterranean wellbore.

4. The method of claim 3, wherein the sealable chamber is a bomb that is released into a tubular body after cement-slurry displacement; and travels down the well by force of gravity.

5. The method of claim 1, wherein the cement slurry is used in the context of primary cementing or remedial cementing.

6. The method of claim 1, wherein the fiber-coil pitch in the spool is greater than the fiber diameter.

7. The method of claim 1, wherein at least one sensor is connected to the second end of the fiber line.

8. The method of claim 1, wherein a Bragg-grating sensor is placed on one end of the fiber-optic line.

9. The method of claim 1, wherein the fixed position is located at the surface of the well.

10. The method of claim 1, wherein the light signal is generated and analyzed by an instrument that comprises a light transmitter and receiver.

11. The method of claim 1, wherein a fiber macrobend radius changes as the cement slurry sets, thereby causing an attenuation of the light signal.

12. The method of claim 1, wherein the device that travels through the tubular body is a cementing plug.

13. The method of claim 1, wherein the desired location is a casing shoe.

14. The method of claim 1, wherein the light-signal wavelength is between 400 nm and 1700 nm.

15. A method of treating a well comprising:
   (i) pumping a cement slurry in a subterranean wellbore;
   (ii) selecting a continuous fiber-optic line having a first end and a second end;
   (iii) securing the first end to a fixed position;
   (iv) securing the second end to a spool, and winding the line around the spool such that there is sufficient line to form at least one coil crossing when set time of the cement slurry is determined;
   (v) immersing the spool in the cement slurry;
   (vi) pumping a volume of cement slurry behind the spool;
   (vii) generating a light signal from the fixed position and transmitting the signal along the fiber-optic line; and
   (viii) measuring changes in the reflected-signal intensity, thereby informing on the state of the cement slurry in which the spool is immersed.

16. The method according to claim 15, further comprising:
   (i) placing the spool in an apparatus for dispensing line;
   (ii) attaching the apparatus to a device that travels through a tubular body in the wellbore, and inserting both inside the tubular body;
   (iii) pumping cement slurry into the tubular body, releasing the device, allowing the device to travel through the tubular body, away from the fixed position, thereby allowing the line to unwind from the apparatus;
   (iv) pumping a volume of cement slurry behind the device such that the apparatus and the spool are immersed in the cement slurry; and
   (v) pumping process fluid behind the cement slurry, and allowing the device to rest at a desired location inside the tubular body.

17. The method according to claim 15, wherein fiber macrobend radius changes as the cement slurry sets, thereby causing an attenuation of the light signal.

18. A method of cementing a well comprising:
   (i) pumping a cement slurry in a subterranean wellbore;
   (ii) selecting a continuous fiber-optic line having a first end and a second end;
   (iii) securing the first end to a fixed position;
   (iv) securing the second end to a spool, and winding the line around the spool such that there is sufficient line to form at least one coil crossing when the set time is determined;
   (v) immersing the spool in the cement slurry;
   (vi) pumping a volume of cement slurry behind the spool;
   (vii) generating a light signal from the fixed position and transmitting the signal along the fiber-optic line; and
   (viii) measuring changes in the reflected-signal intensity, thereby informing on the state of the cement slurry in which the spool is immersed.

19. The method according to claim 18 further comprising:
   (i) placing the spool in an apparatus for dispensing line;
   (ii) attaching the apparatus to a device that travels through a tubular body in the wellbore, and inserting both inside the tubular body;
   (iii) pumping cement slurry into the tubular body, releasing the device, allowing the device to travel through the tubular body, away from the fixed position, thereby allowing the line to unwind from the apparatus;
   (iv) pumping a volume of cement slurry behind the device such that the apparatus and the spool are immersed in the cement slurry; and
   (v) pumping process fluid behind the cement slurry, and allowing the device to rest at a desired location inside the tubular body.

20. The method according to claim 18, wherein fiber macrobend radius changes as the cement slurry sets, thereby causing an attenuation of the light signal.

* * * * *